United States Patent [19]

Wolfson

[11] 4,048,690
[45] Sept. 20, 1977

[54] TWIN-BRUSHES ROTARY TOOTHBRUSH

[76] Inventor: Alan Wolfson, 10340 Fieldcrest Court, Omaha, Nebr. 68114

[21] Appl. No.: 690,607

[22] Filed: May 27, 1976

[51] Int. Cl.² .......................................... A46B 13/08
[52] U.S. Cl. ...................................... 15/22 R; 15/29
[58] Field of Search ............. 15/22 R, 28, 29, 167 A, 15/26, 25; 128/62 R

[56] References Cited

U.S. PATENT DOCUMENTS

| 642,731 | 2/1900 | Swanson | 15/26 |
|---|---|---|---|
| 1,225,955 | 5/1917 | Hickman | 15/167 A |
| 1,580,784 | 4/1926 | Hayden | 15/28 X |
| 3,732,589 | 5/1973 | Burki | 15/22 R |
| 3,984,890 | 10/1976 | Collis | 15/22 R |

FOREIGN PATENT DOCUMENTS

| 43,516 | 8/1910 | Austria | 15/26 |
|---|---|---|---|
| 851,790 | 10/1939 | France | 15/25 |

Primary Examiner—Edward L. Roberts
Attorney, Agent, or Firm—George R. Nimmer

[57] ABSTRACT

Rotary toothbrushes herein disclosed comprise an elongate horizontal tubular barrel with a depending rearward handle. At the barrel forward part is a pair of upright rotary brushes with the bristles extending transversely inwardly toward the barrel and revolvably secured thereto with a common axle means so that the twin-brushes rotate in co-angular unison. There are bi-directional powering means, and preferably manual, to cause the twin-brushes to move in alternating angular directions whereby bucal and lingual sides of upper and lower teeth are simultaneously swept. Specially arrayed bristles promote efficacious sweeping and cleaning to the teeth and gingival surfaces. Aptly positioned stationary brushes might be on the barrel between the rotary brushes. Dental hygiene liquids can be stored within the hollow handle and controllably deliverable therefrom along tubular plumbing having a lead-end extending toward one or both twin-brushes.

12 Claims, 5 Drawing Figures

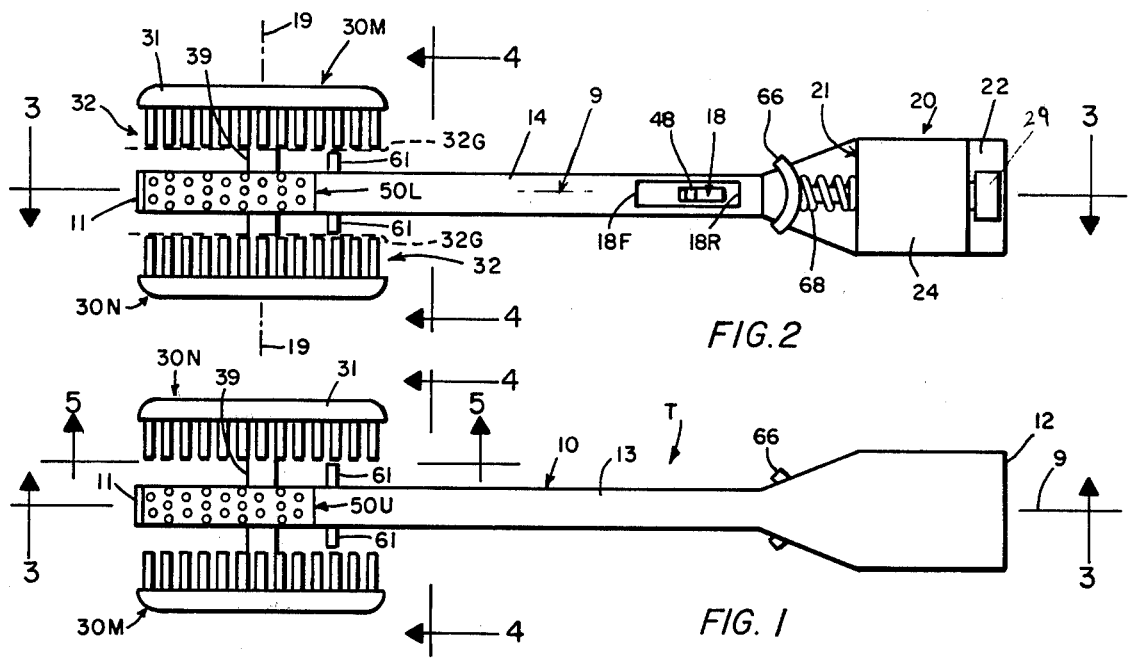
FIG. 2
FIG. 1
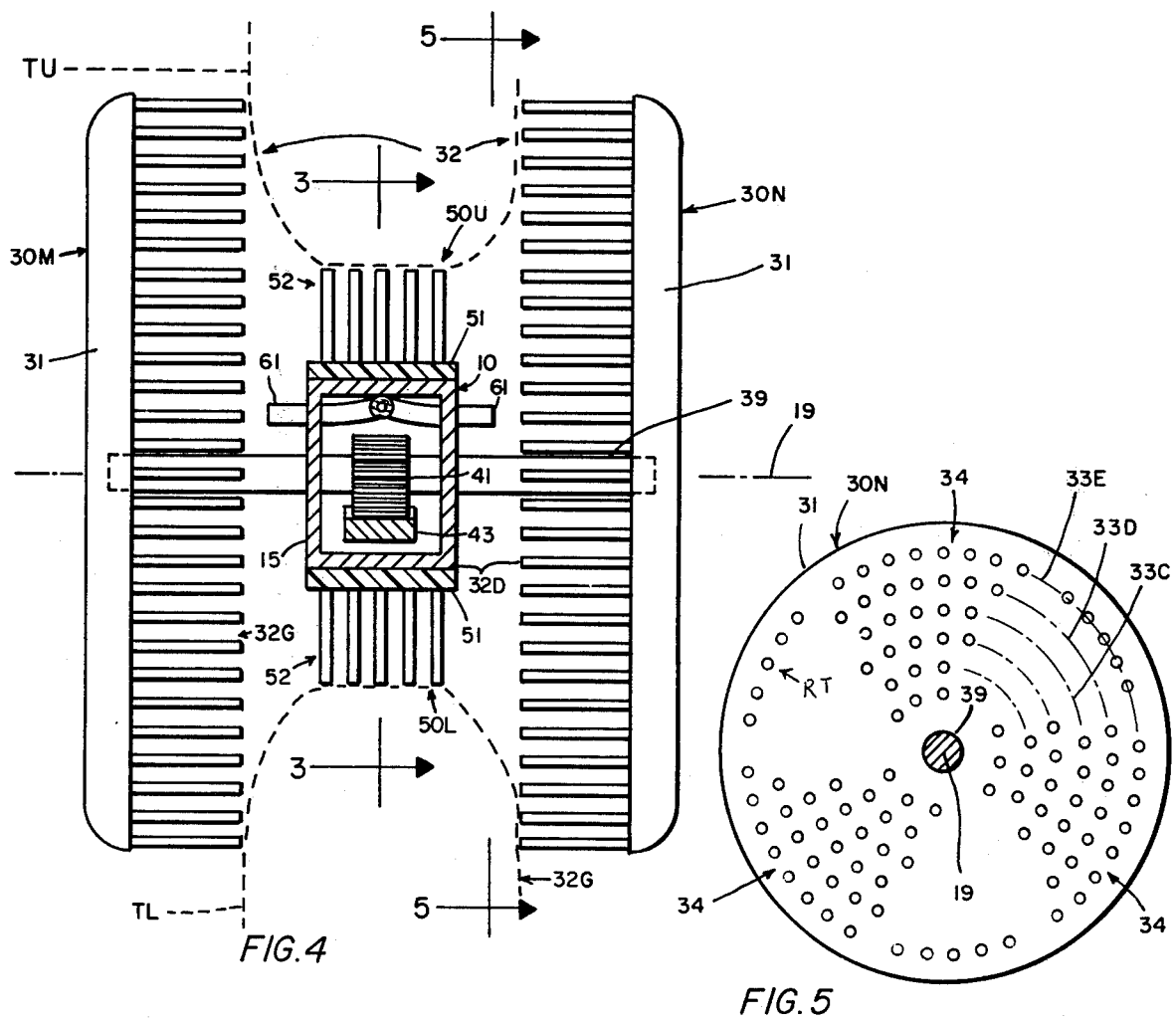
FIG. 4
FIG. 5

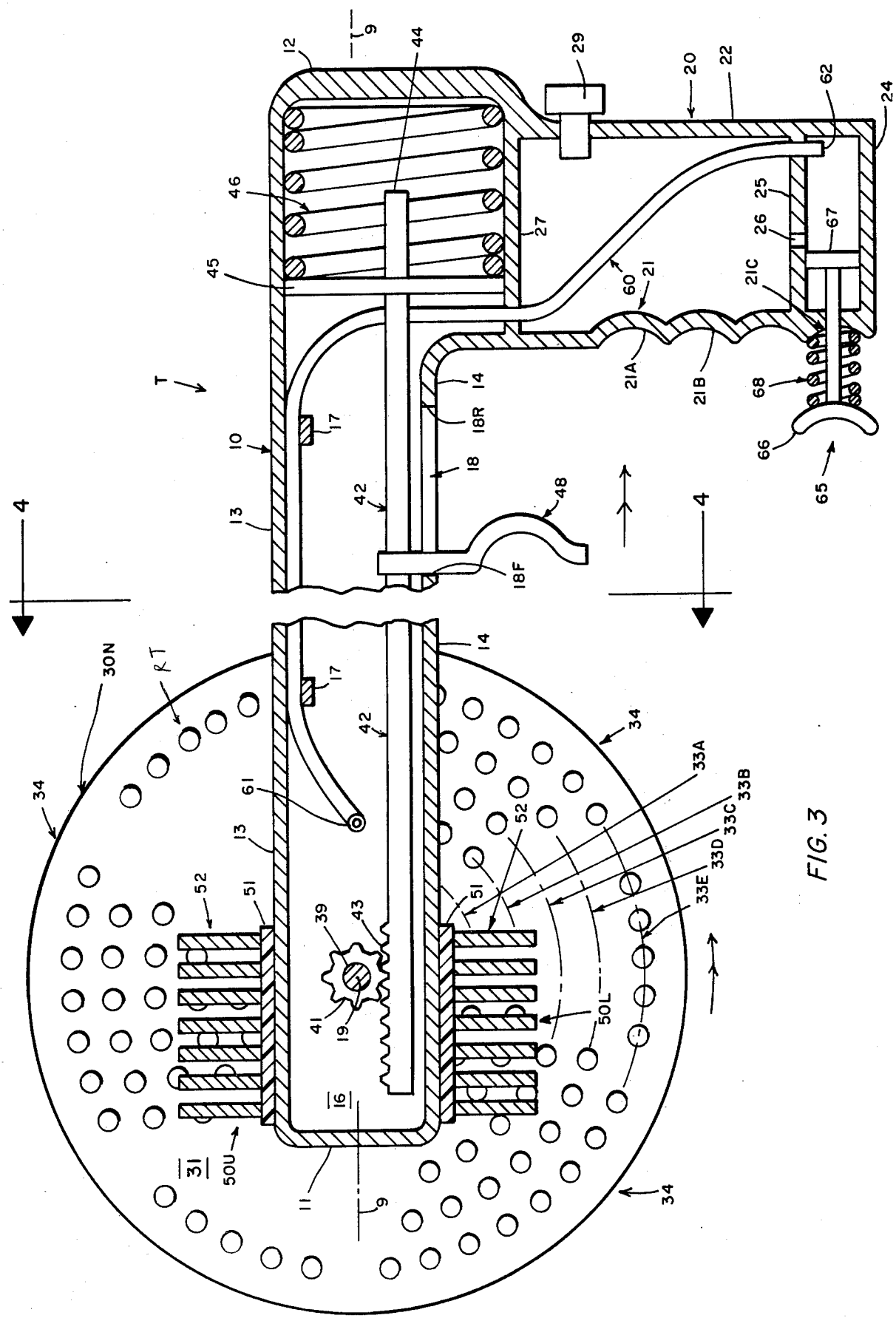

TWIN-BRUSHES ROTARY TOOTHBRUSH

The prior art discloses several configurations for rotary toothbrushes, comprising one or a plurality of rotary brushes. However each of the prior art structures seems to suffer from one or more disadvantages or deficiencies, either structurally, operationally, or in the treatment rendered to the teeth and gingiva.

It is accordingly the general object of the present invention to provide an improved type rotary brushes toothbrush and which overcomes noteworthy structural and dental hygenic disadvantages and deficiencies associated with prior art rotary toothbrushes.

It is an ancillary general object to provide a rotary brushes type toothbrush that performs unusually efficacious treatment for various surfaces of the teeth and the gingiva, and which toothbrush is exceedingly well and adroitly manipulatable and controllable by the operator thereof.

With the above and other objects and advantages in view, which will become more apparent as this description proceeds, the twin-brushes rotary toothbrush generally comprises an elongate horizontal tubular barrel with a rearwardly depending handle to provide a pistol-type grip for the toothbrush, a pair of upright rotary brushes with bristles extending horizontally transversely inwardly toward the barrel forward portion and common axle means extending along a horizontal transverse-axis whereby both brushes are co-angularly rotatable in unison; bi-directional powering means, and preferably manually powered, to effect alternating angular directional movement around the transverse-axis for the twin-brushes; and certain other desireable optional features such as upright stationary brushes located between the rotary twin-brushes, specially arranged patterns for the bristles of the twin-brushes, and elongate plumbing adapted to squirt liquid dental/hygenic fluid (storable in the toothbrush handle) which is controllably deliverable toward the rotary twin-brushes.

In the drawing, wherein like characters refer to like parts in the several views, and in which:

FIG. 1 is a top plan view of a representative embodiment of the twin-brushes rotary toothbrush concept of the present invention;

FIG. 2 is a bottom plan view of the FIG. 1 representative embodiment;

FIG. 3 is a longitudinally extending sectional elevational view taken along lines 3—3 of FIGS. 1, 2, and 4;

FIG. 4 is a transversely extending sectional elevational view taken along lines 4—4 of FIGS. 1, 2, and 3; and FIG. 5 is a sectional elevational view taken along lines 5—5 of FIGS. 1 and 4.

The toothbrush representative embodiment "T" comprises an elongate tubular barrel 10 extending along and surrounding a horizontal longitudinal-axis 9, said barrel 10 including a fore-end 11 and a rear-end 12, and elongate topside 13 and elongate bottomside 14. The preferred barrel 10 is of rectangular cross-sectional shape comprising four longitudinally extending elongate planar panels including a topside panel 13, a bottomside panel 14, a leftside panel 15 and a rightside panel 16. Toothbrush T herein also comprises an upright handle 20 attached to and depending from the barrel rearward portion (i.e. nearer 12 than to 11), said handle 20 comprising an upright frontface 21, an upright rearface 22, and bottomface 24. Providing apt grasping means for the toothbrush operator, handle frontface 21 is provided with a plurality of concave finger-rests such as at 21A, 21B, and 21C. Handle 20 is preferably hollow, to provide a dentifrice fluids reservior, which will be explained later in more detail.

There is a pair of transversely separated upright rotary brushes herein identified as identical brushes 30M (left) and 30N (right). Each of the rotary brushes 30M and 30N comprises an upright support 31 for the numerous parallel bristles 32 which extend horizontally transversely inwardly from support 31 toward barrel 10. The numerous horizontal bristles are seen to have their free-ends lying along an upright imaginary-plane 32G located a small distance (32D) outwardly proximal from the barrel sides 15 and 16. Each of said brushes at support 31 is rotatably secured to the barrel forward part (i.e., nearer 11 than to 12) with a common axle means lying along a horizontal transverse-axis 19 whereby both rotary brushes (30M and 30N) are rotatable only in co-angular unison about said axis 19. Herein depicted for the common axle means is a one-piece horizontal axle 39 passing through and rotatably secured to the barrel panels 15 and 16 and also secured with the geometric center 19 of both upright supports 31, which are preferably of circular disc-like form 31.

There is bi-directional powering means for imparting pulsating alternating angular rotation to the co-angularly unison twin-brushes 30, said powering means preferably extending longitudinally internally of tubular barrel 10. The bi-directional powering means desirably depends upon the toothbrush operator's controllable manual power, such as comprising a longitudinally extending horizontal elongate rack 42 located inside the barrel 10 and cooperating with a pinion 41 for the common axle means. Herein, the center of axle 39 is provided with a pinion 41. Elongate rack 42 has a forward toothed portion 43 underlying and cooperating with the axle pinion 41 and a rearward rack extremity 44. Integrally connected to and surrounding the rack rearward portion, but forwardly of its rearward extremity 44, is a washer 45. Surrounding the rack rearward portion rearwardly of washer 45 is a rearwardly yieldably compressible helical spring 46 which bears against washer 45 and the barrel rear-end 12. The barrel bottomside panel 14 nearer to handle 20 than to fore-end 11 is provided with a longitudinally extending elongate bottom-slot 18. Integrally co-movably attached to rack 42 and depending therefrom through 18 is a trigger 48 which is normally urged toward the slot front-end 18F by spring means 46. Thus, when the operator manually grasps handle 20, and with the index-finger pulling rearwardly on trigger 48 to the slot back-end 18R, then as indicated in double-headed curved arrow in FIG. 3, rotary brushes 30 rotate in the counterclockwise direction. Then, as the operator manually releases trigger 48, spring 46 moves rack 42 forwardly whereby trigger 48 moves to slot front-end 18F, and the rotary brushes move in the clockwise direction. This alternating angular movement of unison rotating brushes 30M and 30N occurrs each time the operator depresses and then releases trigger 48. Thus, the bucal and lingual sides of the operator's upper and lower teeth receive bi-directional brushing each time the operator depresses and then releases the trigger 48.

In the vein of the bi-directional rotary brushing for the bucal and lingual sides of the operator's upper "TU" and lower "TL" teeth, special arrays of rotary brush bristles 32 are desireable. For one, the bristles 32 are preferably arranged in concentric rings loci (e.g. five loci 33A to 33E) pattern and having said horizontal axle (e.g. 19, 39) as the geometric center. In addition, the concentric rings array is preferably further confined within a plurality of identical cusp-shaped fields 34 (herein three in number on each rotary brush 30). This provides an efficaceous pulsating bi-directional sweeping action between neighboring teeth and avoids debris compaction therein which has plagued prior art rotary toothbrush structures.

In addition to the rotary twin-brushes 30, there is preferably also a pair of stationary brushes 50 attached to the barrel 10 forward portion, including a top-brush 50U and a bottom-brush 50L. Each brush 50 includes a horizontal base 51 which is attached to the barrel respective panels 13 and 14 and a plurality of vertical bristles 52. It will be noted that brushes 50 are preferably of identical shape, size, and longitudinal location along barrel 10 between brushes 30. Thus, for example, along the upper "TU" and lower "TL" teeth rows, rotary brush 30M scrubs the bucal side of both rows, rotary brush 30N scrubs the lingual side of both rows, top-brush 50U scrubs the occlusial surface of row "TU", and bottom-brush 50L scrubs the occlusial surface of row "TL", the said six teeth surfaces being scrubbed simultaneously when the operator adroitly reciprocates trigger 48 and barrel handle 20. In this regard, as best seen in FIGS. 2 and 3, stationary brushes bristles 52 are sufficiently short length to terminate in elevation below the concentric outward loci 33 for bristles 32.

As was previously mentioned, handle 20 is preferably hollow to provide a fluids reservoir for dentifrice, mouthwash, etc. Handle rearface 22 is apertured including a removable plug 29 therefor to permit charging of the desired fluid into handle 20. To deliver the fluid, there is elongate tubular plumbing 60 including a trail-end 62 communicating within hollow handle 20 and at least one lead-end 61 extending transversely toward one or both the rotary brushes 30. Herein, the plumbing line 60 lies along and within tubular barrel 10 and has a bifurcate forward portion to provide two lead-ends 61, directed outwardly through barrel sides 15 and 16 to supply liquid onto both rotary brushes 30. To enhance delivery of fluid stored within handle 20, handle 20 internally includes a pair of fluid-impervious horizontal walls such as upper-wall 27 and lower-wall 25 having a tiny hole 26. Upper-wall 27 is located immediately below, and helps to support, helical spring 46. Lower-wall 25 is spaced a small finite distance above handle bottom-face 24 with the tubing trail-end 62 being located therebetween. Tubing 60 proceeds upwardly through lower-wall 25, thence upwardly through upper-wall 27, and thence horizontally within barrel 10 (but not interfering with rack 42, as by virtue of barrel internal clips 17). Horizontal piston 65 passes through handle frontface 21 at 21C. Piston 65 includes an enlarged shoulder 67 tightly slidably disposed between lower-wall and bottom-face 24, and also a concave finger pad 66, helical spring 68 surrounding piston 65 between pad 66 and the handle frontface at 21C. Thus, each time pad 66 is depressed by the operator's finger, fluid from between walls 24 and 25 is forced into the tubing trail-end 62 and squirts from the lead-end 61 to supply the rotary brush 30.

Although having already been alluded to, operation of the toothbrush embodiment T might be summarized as follows. It will be assumed that the operator wishes to treat his own teeth and gums, and that the operator is right-handed with his right index finger engaged with trigger 48 and with his right little finger available to depress the piston pad 66. At the outset, if the operator wishes, he might put a dentifrice of his own selection (independent from plumbing 60) onto the bristles 32 and 52. Then, the operator brings the occlusial surface of his teeth rows "TU" and "TL" fairly firmly upon the bristles 52, whereby one brush 30 contacts the lingual sides and the other brush 30 contacts the bucal sides of both teeth rows "TU" and "TL". Then, slowly moving the apparatus T so that bristles contact along both rows "TU" and "TL", the operator repeatedly depresses trigger 48 toward slot rear 18R, each depression being followed by a trigger release toward slot front 18F. These trigger reciprocations cause brushes 30 to rotate in co-angular unison in alternating angular directions, and unnecessary to exceed about 240° each time. The preferably cusp-shaped bristles fields 34 facilitate the sweeping action. To further enhance sweeping, the central bristles of each locus 33 might be slightly lengthier. The outer circular bristles locus 33E might extend between the fields 34 as bristles "RT" to retard outward fluid flow. Periodically, between manipulations of trigger 48, the operator might depress plunger 65 to cause additional fluid to be emitted from plumbing 60 at 61, onto bristles 32. Upon conclusion of the teeth and gingiva cleaning operation, the operator can rinse bristles 32 and 52 in conventional fashion, and add hygenic fluid through removable plug 29.

From the foregoing, the construction and operation of the twin-brushes rotary toothbrush will be readily understood and further explanation is believed to be unnecessary. However, since numerous modifications and changes will readily occur to those skilled in the art, it is not desired to limit the invention to the exact construction shown and described, and accordingly, all suitable modifications and equivalents may be resorted to, falling within the scope of the appended claims.

I claim:
1. A twin-brushes rotary toothbrush comprising:
   A. a horizontally longitudinally extending elongate tubular barrel having a fore-end and a rear-end, and longitudinally horizontally extending elongate topside and bottomside;
   B. handle means at the barrel rearward portion;
   C. a pair of transversely separated upright rotary brushes, each of said brushes comprising an upright support rotatably secured to the barrel forward portion with a common axle means lying along a horizontal transverse-axis whereby the two brushes are rotatable in co-angular unison about said transverse-axis, each of said rotary brushes comprising an array of horizontal bristles extending transversely inwardly from the brush upright support toward the barrel, the free-ends of the bristles lying along an upright imaginary-plane located proximally outwardly said barrel; and
   D. bi-directional powering means for imparting coangular rotation to the rotary brushes in pulsating alternating angular directions about said horizontal transverse-axis, said bi-directional powering means extending along said barrel.

2. The twin-brushes toothbrush of claim 1 wherein the handle is upright and extends downwardly from the barrel; wherein the barrel bottomside adjacent the handle is provided with a longitudinally extending elongate bottom-slot; wherein there is an upright trigger disposed within the barrel and extending downwardly through said elongate bottom-slot; wherein the upright support for each rotary brush is of a circular disc-like form and the bristles array is arranged in a concentric rings loci pattern and having said transverse-axis as the geometric center; and wherein the bi-directional powering means is located inside the barrel and comprises a longitudinally extending horizontal rack attached to the trigger and the rack also cooperating with a pinion means on the said common axle means for rotating said pair of brushes, the rearward portion of said rack being against spring means located inside said tubular barrel.

3. The twin-brushes rotary toothbrush of claim 2 wherein the forward portion of the barrel topside and bottomside between said pair of brushes are each provided with stationary brushes, the top-brush extending upwardly from the barrel topside and the bottom-brush extending downwardly from the barrel bottomside, the upright length of the stationary brushes' upright bristles being sufficiently arrested that it is less than the distance of that most remote circular locus of the rotary brush from said horizontal transverse-axis.

4. The twin-brushes rotary toothbrush of claim 3 wherein the array of concentric rings bristles for each rotary brush are further arranged in a plurality of distinct cusp-shaped fields.

5. The twin-brushes rotary toothbrush of claim 2 wherein the handle includes a fluid reservoir, there being elongate plumbing including a trail-end communicating with said reservoir and at least one lead-end extending transversely toward the rotary brush bristles.

6. The twin-brushes rotary toothbrush of claim 5 wherein the elongate plumbing medial portion lies along the tubular barrel and supported therewithin by barrel internal clips, said plumbing being forwardly bifurcate to provide two lead-ends.

7. The rotary toothbrush of claim 6 wherein the handle includes a finger-operated plunger located beneath said trigger, said plunger being adapted to inject fluid from said reservoir and to squirt said fluid from the plumbing lead-ends; and wherein the handle is provided with a removable plug for introducing hygenic fluid into the handle reservoir.

8. The twin-brushes rotary toothbrush of claim 1 wherein the bristles array for each rotary brush is arranged in a concentric rings loci pattern with the said transverse-axis as the geometric center, said bristles array being further confineably arranged in a plurality of cusp-shaped fields.

9. The twin-brushes rotary toothbrush of claim 8 wherein central bristles of each concentric rings locus are slightly transversely lengthier than are the flanking bristles; and wherein an outer circular locus between the cusp-shaped fields is equipped with bristles to retard outward flow of the hygenic fluid.

10. The twin-brushes rotary toothbrush of claim 1 wherein the barrel bottomside nearer the handle means than to the transverse-axis is provided with a longitudinally extending elongate bottom-slot; and wherein there is a trigger extending downwardly through the said elongate bottom-slot; and wherein the bi-directional powering means comprises a longitudinally extending rack located inside the barrel and attached to said trigger, the rack forward portion cooperating with a pinion means on the said common axle means.

11. A twin-brushes rotary toothbrush comprising:
A. a horizontally longitudinally extending elongate barrel having a fore-end and a rear-end, and longitudinally horizontally extending elongate topside and bottomside;
B. handle means at the barrel rearward portion;
C. a pair of separated upright rotary brushes, each of said rotary brushes comprising an upright support rotatably secured to the barrel forward portion with a common axle means whereby the two brushes are rotatable in co-angular unison, each of said rotary brushes comprising an array of horizontal bristles extending from the brush upright support toward and facing the bristles of the other rotary brush, whereby simultaneously the bristles of one rotary brush are adapted to sweep the bucal sides and the bristles of the other rotary brush are adapted to sweep the lingual sides of the upper and lower rows of the operator's teeth;
D. bi-directional powering means for imparting coangular rotation to the rotary brushes in pulsating alternating angular directions, said bi-directional powering means extending along said barrel; and
E. horizontally extending brushing surfaces located between the upright rotary brushes and parallel to the common axle means for contacting the occlusial sides of the upper and lower teeth.

12. the twin-brushes rotary toothbrush of claim 11 wherein the handle includes a fluid reservoir, there being elongate plumbing including a trail-end communicating with said reservoir and at least one lead-end extending transversely toward the rotary brush bristles.

* * * * *